United States Patent
Friauf

Patent Number: 5,865,753
Date of Patent: Feb. 2, 1999

[54] COHERENT DETECTION ULTRASOUND SYSTEM

[76] Inventor: Walter S. Friauf, 5616 Oakmont Ave., Bethesda, Md. 20817

[21] Appl. No.: 863,983

[22] Filed: May 27, 1997

[51] Int. Cl.$^6$ .................................................. A61B 08/00
[52] U.S. Cl. ............................................................ 600/455
[58] Field of Search ................................. 600/455, 456, 600/454

[56] References Cited

U.S. PATENT DOCUMENTS

| | | | |
|---|---|---|---|
| 5,398,216 | 3/1995 | Hall et al. | 600/454 |
| 5,437,281 | 8/1995 | Lin et al. | 600/455 |
| 5,443,071 | 8/1995 | Banjanin et al. | 600/455 |
| 5,474,073 | 12/1995 | Schwartz et al. | 600/456 |

*Primary Examiner*—Marvin M. Lateef
*Assistant Examiner*—Maulin Patel

[57] ABSTRACT

An ultrasound imaging system that utilizes a short sinusoidal pulse burst for excitation, and performs coherent detection of the reflected signal, resulting in improved signal-to-noise ratio. In addition, the polarity of the rate of change of parameters, principally density, is preserved by the coherent detection. This allows a density versus distance signal to be reconstructed by integrating the coherently detected signal. The system includes components to calculate and apply all necessary phase corrections.

11 Claims, 5 Drawing Sheets

COHERENT DETECTION ULTRASOUND SYSTEM

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

BACKGROUND OF THE INVENTION

This invention relates to non-invasive ultrasonic measurement of properties of materials by a pulse echo technique, as in seismology, sonar, and medical imaging. More particularly, the present invention relates to the production of a two dimensional image of the density of physiological material when a sector scan or other type of two dimensional scan is used for medical diagnosis.

Pulse echo techniques for non-invasive determination of the properties of materials have been developed for many fields, including radar, sonar, seismology, and medical diagnostic ultrasound. The following discussion will relate specifically to the last of these, and even more specifically to a system intended to produce an image of a plane section by means of a raster scan. A typical sector scan geometry is shown in FIG. 1. Component 1 comprises the bulk of the ultrasound system, including the final display or print out device, and 2 is the ultrasonic transducer. Element 3 is the physiological system being scanned. For the sake of simplicity, it will be assumed that 3 consists of two volume regions, 3a and 3b, with differing parameters, but that the parameters are uniform within each region. To produce a two dimensional planar image, a number of closely spaced line scans are made sequentially, in a plane, by slightly changing the angle of the transducer between successive lines. The result shown in FIG. 1 is a sector scan, but other types of raster scan are also possible.

The process of producing a signal for each line in turn is identical, and the following discussion will pertain to the single line containing points A and B. The portion of the system shown as 1 in FIG. 1 is shown in more detail in FIG. 2. A pulse generator, 4, generates short excitation pulses spaced farther apart in time than the time required for all reflections from one pulse to arrive back at the transducer. The pulses pass through a transmit/receive switch, 5, to a transducer, 6, which converts the electrical pulse to an acoustic pulse which is directed into the material under study. The acoustic pulse, suitably focused, propagates through the material in approximately a straight line, governed by the wave equation. There is attenuation with distance, but no reflection so long as the properties of the material are uniform. For liquids, the density and one elastic constant, compressibility, determine the main features of the propagation. Although seeming to be a considerable over simplification for most physiological systems, analysis with these parameters is often reasonably satisfactory. A better model for anisotropic solids requires another elastic constant, shear modulus. For isotropic solids, such as muscle, more elastic constants are required, up to a theoretical total maximum of 21. In all cases, another constant representing a dissipation factor, determines the attenuation.

Exact analysis is virtually impossible with the complex geometry encountered in physiological imaging, but fortunately it is unnecessary because of two general considerations. The first is that, irrespective of the number of parameters, when any change in the value of density or elastic constants is encountered, as at point A, a fraction of the incident energy will be reflected back toward the transducer, where it is converted back to an electrical signal. This proceeds through the transmit/receive switch to an amplifier, 7, which uses programmed or automatic gain control, or both, to maintain the amplitude of reflections from identical changes in parameters at different depths approximately constant despite the effect of attenuation. A detector, 8, senses the envelope of the reflected pulse and it is stored and/or displayed as a function of the time following the excitation pulse. Only a display is shown in FIG. 2. The second general consideration is that the change in velocity caused by the change in material parameters that give rise to useful reflections is fairly small, so long as there is no bone or air in the path. Consequently, since the approximate velocity is known, the time between the excitation and the return of a reflection can be interpreted as being proportional to the distance from the transducer to the point at which a change in parameters caused the reflection. Reflections from deeper points, such as B, arrive at later times, and the complete set of reflections from one pulse, two in this example, result in the signal shown on the display, 9. Similar displays for the other scan lines, properly positioned on the display, provide an outline of region 3b. For the sake of simplicity, changes in material parameters will henceforth be referred to as changes in density, although changes in elastic constants may also contribute. The image, although resulting from changes in density, is not an image of density versus position. Rather, it is an image of the absolute value of the derivative of density in the direction of propagation of the ultrasonic wave. For most purposes an image of density would be more desirable, but it cannot be obtained by integrating along the direction of propagation. That is because the value of the reflection, including polarity, would have to be integrated to provide density, but the envelope detection gives only the absolute value of the derivative.

BRIEF SUMMARY OF THE INVENTION

It is accordingly one object of the present invention to provide a means for detecting reflections so as to preserve the polarity, ie, whether the reflection was caused by a transition from a given density to a higher density, or by a transition from a given density to a lower density.

Another object of the present invention is to provide a system that displays a two dimensional reconstruction of the density of material within an object, such as a human body.

A further object of the present invention is to realize an improvement in signal-to-noise ratio of the final image by virtue of coherent detection, also referred to as synchronous detection, which has long been utilized in lock in amplifiers for the same purpose.

According to these and further objects of the present invention which will become apparent as the description thereof proceeds, the present invention provides an ultrasonic system which includes:

an oscillator;

a timing and gating circuit to generate excitation pulses;

a transmit/receive switch to route excitation and reflected pulses;

a transducer to convert the electrical excitation pulses to acoustic pulses, and to convert the reflected acoustic pulses back to electrical pulses;

means for changing the angle or position of the transducer or ultrasonic beam to produce a sector or other type of raster scan;

means for coordinating the display geometry with the scan geometry so as to produce a geometrically correct image;

a programmed gain amplifier to amplify the reflected pulses and to maintain the amplitude of reflections representing a given percentage change in density constant despite the differing effect of attenuation on reflections occurring at different depths;

a sub-system for developing and storing the phase information needed for coherent detection of the reflected signals;

a sub-system for utilizing stored phase information to provide coherent detection of the reflected signal;

an integrator for converting the coherently detected signal to a density profile;

a sub-system for displaying the density information in two dimensions.

BRIEF DESCRIPTION OF THE SEVERAL VIEWS OF THE DRAWING

The present invention will be described with reference to the attached drawings which are given by way of non-limiting examples only in which.

DETAILED DESCRIPTION OF THE INVENTION

For the sake of clarity, the explanation of the operation of the invention will be based on several simplifying assumptions. First, it will relate to reflections from an abrupt transition from one set of material parameters to another set, as at point A or point B in FIG. 1. The results for such a transition contain all the information needed to find the results for any other parameter profile, by appropriate application of the superposition theorem. Second, the discussion will relate to the production of a single static image, so that the processing does not need to be performed in real time. However, by speeding up all the processing sufficiently that additional images can be produced in rapid succession, a dynamic image can be produced without any fundamental changes in the process. Third, an arbitrary explicit excitation waveform consisting of two complete cycles of a sine wave, beginning when the signal goes through zero in a positive direction, will be assumed, although more cycles could be used. Finally, for the explanation of the first stage of processing, constant velocity of propagation of the ultrasonic wave will be assumed.

Figure 2:
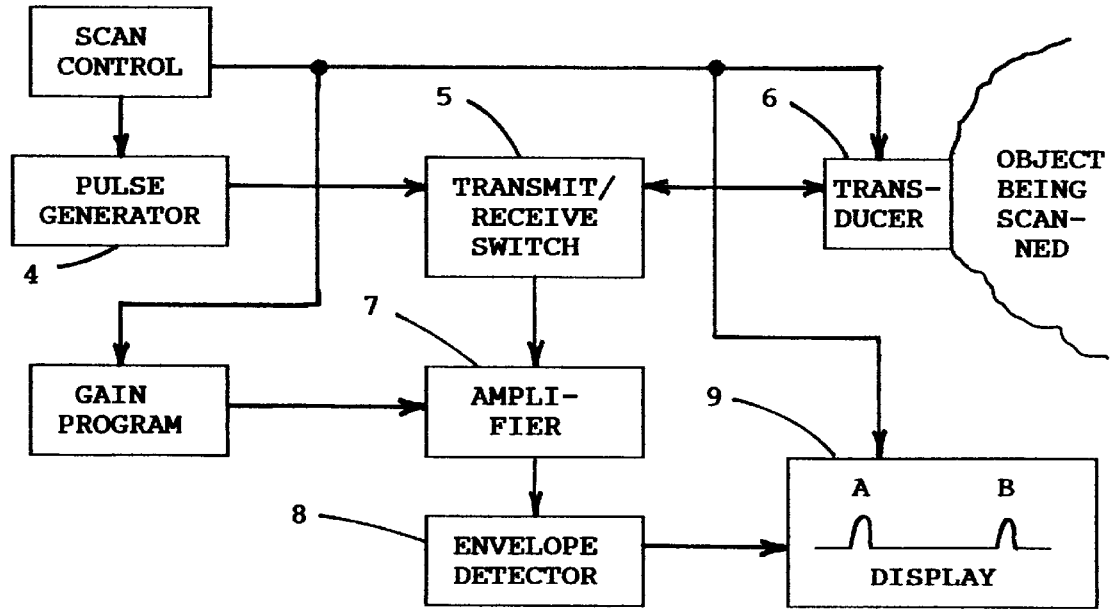
FIG. 2 is a block diagram showing the major components of a conventional ultrasound system.
Figure 3:
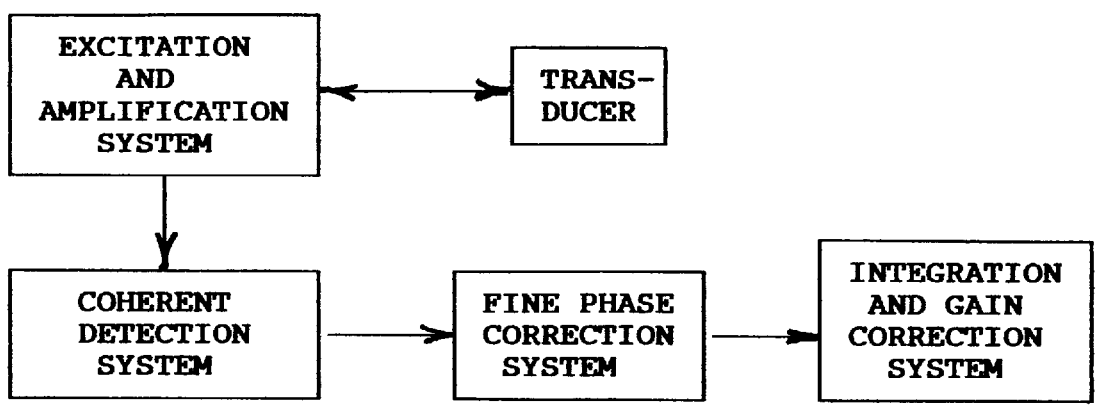
FIG. 3 is a block diagram of an ultrasound system intended to produce two dimensional images of density in a plane within a physiological object such as a human being according to one embodiment of the present invention.

The block diagram of a system for producing a two dimensional image of the density of material within an object being scanned, according to one embodiment of the present invention, is shown in FIG. 3. The scan control functions and the display functions for this system are substantially the same as those in a conventional state-of-the-art medical diagnostic ultrasound system such as the system shown in FIG. 2, and accordingly have not been shown in FIG. 3.

Figure 4:
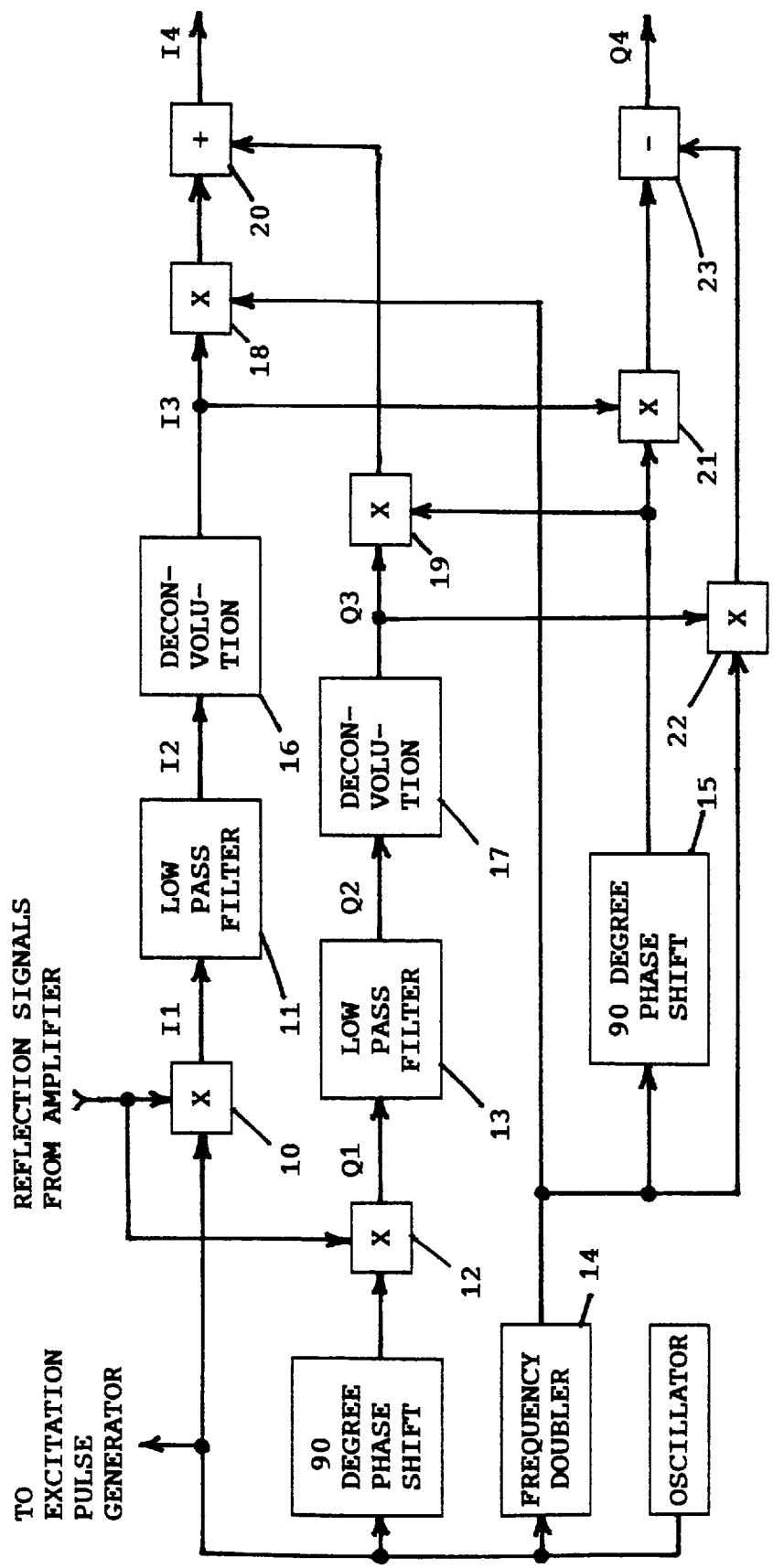
FIG. 4 is a block diagram of a sub-system that accomplishes the first stage of coherent detection according to one embodiment of the present invention.

The first departure from the conventional state-of-the-art is the coherent detection illustrated in FIG. 4. The reflected signal, $A \sin(2\pi ft+\phi)$ within the confines of the pulse gate or envelope, is multiplied by the reference sine wave from the oscillator. This operation can be performed by an analog multiplier, 10. Alternatively, the reflected signals could be digitized by an analog-to-digital converter at a prior point, as early as immediately after the transmit/receive switch, with subsequent operations performed digitally in a computer or any other type of digital signal processor. A is the amplitude of the reflected signal and $\phi$ is its phase relative to the reference sine wave. The output from the multiplier, 10, is designated I1, for IN PHASE AS INITIALLY DETECTED. It is $$[\sin (2 \pi ft)][A \sin (2\pi ft+\phi)] = (A/2) \cos \phi - (A/2) \cos (4\pi ft+\phi) \quad \text{[Equation 1]}$$

within the gate interval, and is zero elsewhere. The second term, at twice the oscillator frequency, is unwanted and is removed by a low pass filter, 11, leaving the first term, which is proportional to the amplitude A of the reflection, and to the cosine of the phase $\phi$ between the reflected signal and the sine wave from the oscillator. The signal at this point is labeled I2. Although coherently detected, this signal, as it stands, is useless, since the phase of the reference sine wave relative to the reflected signal will generally not be what is needed, for two reasons, the second of which will be discussed in connection with the next stage of processing.

Figure 5:
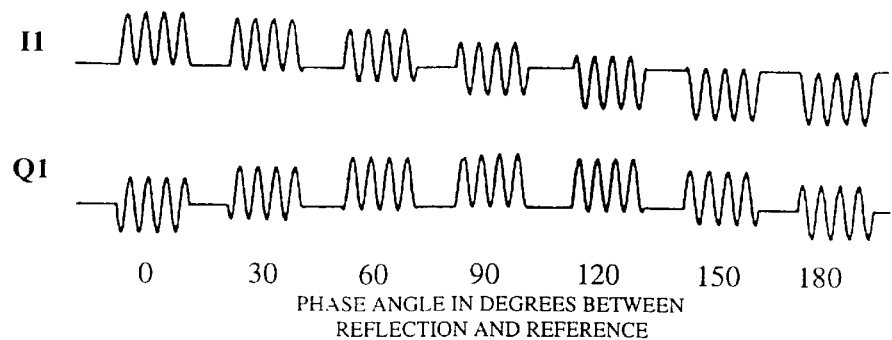
FIG. 5 shows waveforms for reflections from identical material transitions at different distances from the transducer.

The first problem is the continuous shift in the phase of the reflected pulse due to the time delay caused by propagation of the acoustic pulse from the transducer to the point of reflection and back to the transducer. The phase shift, $\phi$, in radians, is $2\pi fT$, where f is the frequency of the sine wave, and T is the delay time. If the velocity of propagation is v, the delay for the round trip will be $T=2d/v$, where d is the distance from the transducer to the point at which the reflection takes place. Combining these two relations, the phase shift of a signal reflected from an interface at depth d is found to be $\phi(d)=4\pi fd/v$. When this value of $\phi$ is substituted into Equation 1 above, it is apparent that the amplitude and polarity of the detected signal depends on the location of the interface, a dependence which is unwanted. This effect is shown in FIG. 5, where the result of coherent detection is shown for several reflections from identical changes in density located at different distances from the transducer. Each increment in distance used for illustrative purposes in FIG. 5 includes a small fraction of a wavelength, to show the resulting phase shift, plus an integral number of wavelengths that do not result in any phase shift, but were included for this figure to keep the several reflections from overlapping.

Since the amplitude of the I2 signal varies sinusoidally with distance, it goes through zero twice each wavelength, resulting in complete loss of information about reflections from those points. However, the information at and around those points will be present in a quadrature signal, Q1, which stands for QUADRATURE SIGNAL AS INITIALLY DETECTED. This signal is detected exactly the same as I1 except with a reference sine wave that is shifted $\pi/2$ radians relative to the reference sine wave used to coherently detect I1. This operation is performed by 12 and 13 in FIG. 4. By suitably combining information from the two signals, dependence on the distance to the point of reflection can be removed from the detected signal.

However, the situation is not quite as simple as it might seem for two reasons. In the first place, the angle used to effect the recombination must be $4\pi ft$ instead of the argument of the excitation sine wave, $2\pi ft$. That is because of the doubling of travel time occasioned by the round trip that reflections have to make. This problem is easily solved by simply doubling the frequency of the reference sine and cosine waves used for the recombining, with components 14 and 15. Again, these could be analog components, or the required values of the trigonometric functions could be computer generated in several ways.

The second problem is much more serious. The zero frequency component of the I1 and Q1 signals persists for approximately the duration of the excitation waveform. During this time the values of the $\sin(4\pi ft)$ and $\cos(4\pi ft)$ waves go through several complete cycles, so that direct multiplication would result in approximately zero average value output, regardless of the average values of I1 and Q1. This is because the average value of a sine wave, over an integral number of cycles, is zero. To overcome this problem, it is necessary to convert the I2 and Q2 signals approximately to the shape of delta functions, using 16 and 17. The label "deconvolution" is used for these components because it describes the type of processing needed, even though the signals are not the result of a corresponding convolution process. Exact deconvolution is impossible, but fortunately it is also unnecessary since sine and cosine functions vary rather slowly in the neighborhood of their maximum value. The deconvolutions can be effected with hardware, such as a delay line, with the values from suitably weighted taps summed. It can also be performed in a similar fashion digitally in a computer. Alternatively, the signals can be Fourier transformed into the frequency domain, the amplitude function multiplied frequency by frequency by the values of an appropriate deconvolution kernel, with a corresponding modification of the phase function, followed by inverse Fourier transformation back into the time domain. Although the deconvolution can be done many ways, the most practical, in view of the drastic shortening required, is by a computer working in the frequency domain. It is also possible that the shortening could be accomplished with other types of signal processing.

Since the preceding low pass filtering operation is a convolution operation, it can be consolidated with the deconvolution by combining the kernels needed for both operations.

While on the subject of deconvolution, it should be mentioned that the waveform of the reflected signal has been assumed to be identical to that of the excitation signal, implying that the transfer function of the ultrasonic transducer and its acoustic coupling to the subject being scanned, is unity. This will never be exactly the case, so that it may be necessary to effect some improvement of the waveform of reflected signals by another appropriate deconvolution immediately after the amplifier. A correction for the effect of dispersion may also be desirable at this point. Although the effect of dispersion is reduced by the use of a sinusoidal excitation pulse, the effect is not eliminated because of the shortness of the pulse.

The waveshape of the difference frequency component of the I1 and Q1 signals, aside from amplitude and polarity, changes slightly with the position of the reflection, so that a fixed kernel cannot provide optimum deconvolution for all reflections. However, the changes are sufficiently minor that this is not a serious problem, and a fixed kernel can be used satisfactorily. Nevertheless, the deconvolution process is one of the most difficult of all the steps. The excitation signal chosen for illustrative purposes, two cycles of a sine wave, results in I2 and Q2 signals that must be compressed in time by a factor of approximately ten or more to give outputs, I3 and Q3 respectively, that are short enough that the multiplying functions at twice the excitation frequency will be reasonably constant during the multiplication. This condition will be approached least well when the multiplying functions are changing fastest, but this will be when they are very small so that the departure from perfect deconvolution will have little adverse effect.

Such a severe deconvolution markedly degrades signal-to-noise ratio, but this is acceptable because of excellent signal-to-noise ratio prior to deconvolution, due to the coherent detection, and the improvement realized later by the integration that is made feasible by preserving the polarity of reflections. The integration also greatly reduces the effect of unavoidable ripple on both sides of the peak of I3 and Q3.

The I3 and Q3 signals are multiplied by the double frequency sine and cosine functions respectively to provide signals which, when summed, provide a signal, I4, proportional to the rate of change of material parameters in the direction of propagation. The multiplication and summing functions are performed by 18 through 20 in FIG. 4. As always, these can be either hardware components or software operations.

To review the operation of the invention up to this point, the reflected signal has been coherently detected by multiplying it by a continuous sine wave from the oscillator used to generate the excitation pulse. The coherent detection preserves the polarity of reflections, which gives the polarity of the rate of change of material parameters. In addition, however, the coherent detection gives a sinusoidal dependence of the detected signal on the position at which a reflection occurs. This dependence is undesirable, but it can be removed because the time at which the reflection arrives back tells where the reflection occurred, allowing correction for the dependence. However, the dependence on position is extremely rapid, so that the determination of the position of a reflection from the time of arrival must be extremely accurate. This has not been a problem in the discussion so far, because exactly constant velocity has been assumed. In practice, this will not be the case, because the changes in parameter values giving rise to reflections will also modify the velocity of propagation somewhat. As mentioned earlier, the modification is slight, so that the resulting image distortion is acceptable, but the modification is still sufficient to give a phase function that differs considerably from the perfectly linear phase function calculated assuming constant velocity.

Figure 6:
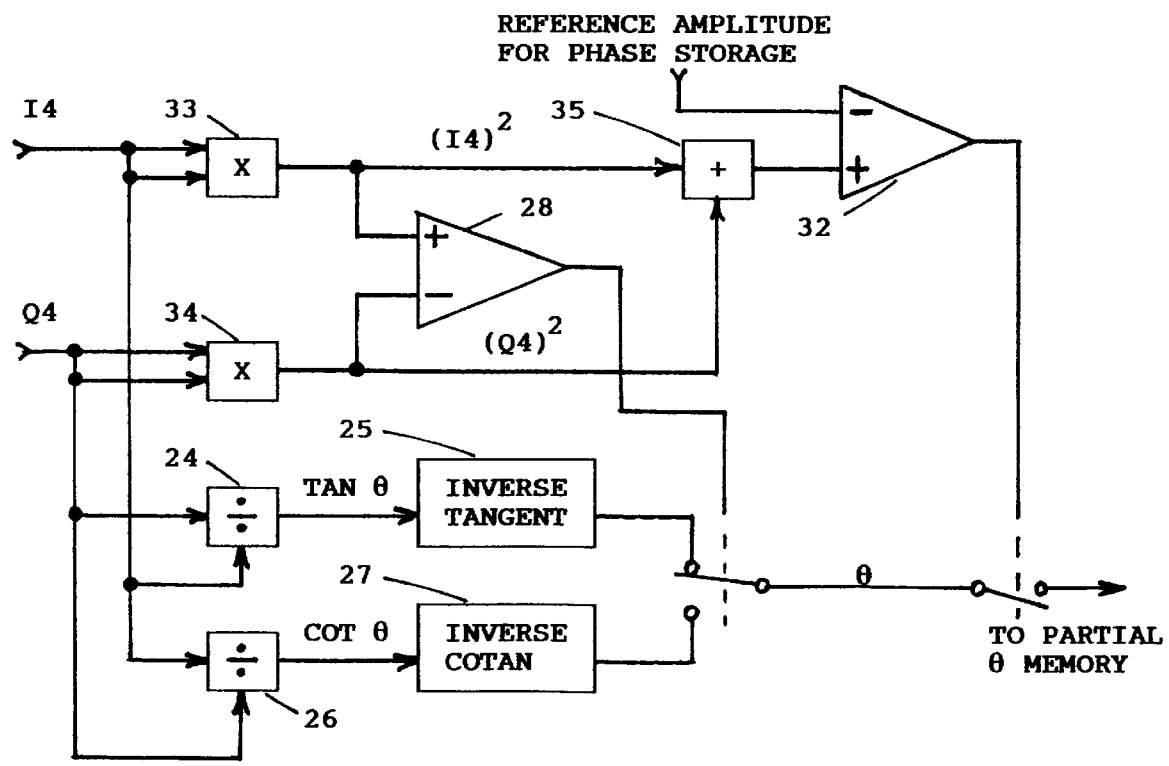
FIG. 6 is a block diagram of a sub-system that determines the phase of reflected signals at major interfaces.
Figure 7:
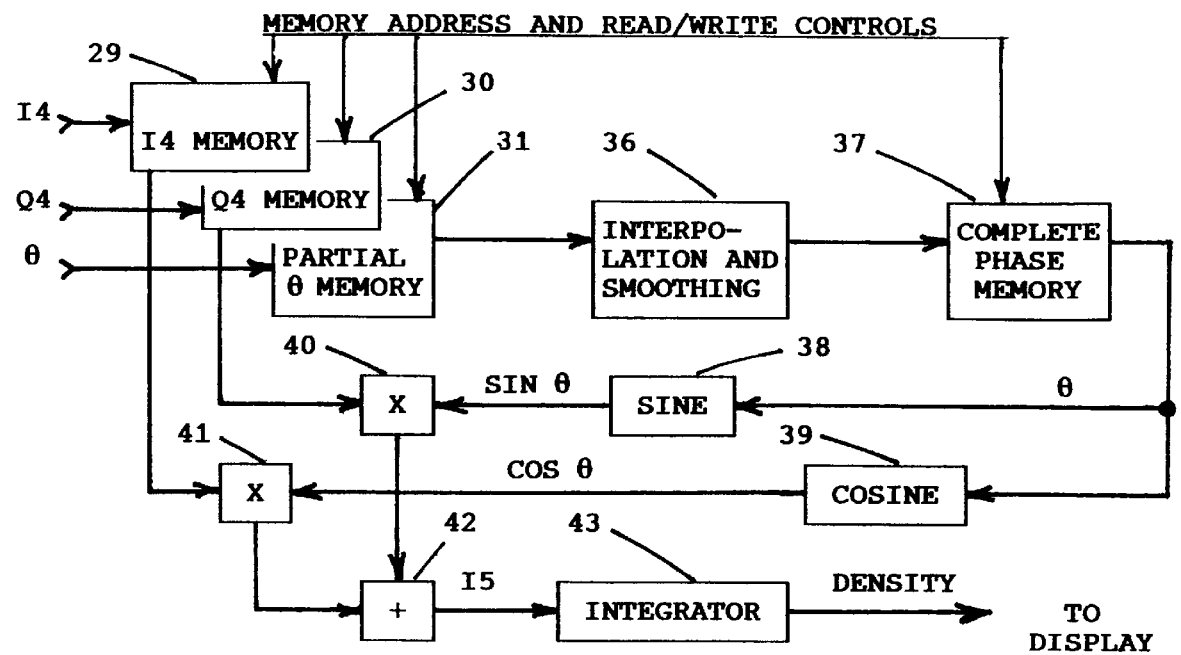
FIG. 7 is a block diagram of a sub-system that performs the final fine phase correction based on the measured values of phase at major interfaces, and integrates the value of phase-corrected reflections so as to provide an image of density.

FIG. 6 and FIG. 7 are block diagrams of two sub-systems that deal with this problem, according to one embodiment of the present invention. The inputs to these subsystems include I4, which has been discussed before, and Q4, which was not discussed because, under the assumption of absolutely constant velocity of propagation, it would always be zero, and hence unneeded. However, it will be needed in general, and is developed by 21 to 23 in FIG. 4, in a manner analogous to that described for I4. The output of multiplier 22 is subtracted from the output of multiplier 21, rather than added, in order to obviate the need for another 90 degree phase shifter between the reference inputs to 21 and 22. The other input to the sub-system of FIG. 7 is scan information, which is necessary for the ultimate construction of an image with correct geometry.

The general idea of the processing shown in FIG. 6 is to determine an angle $\theta$ which, when used to calculate values of I5 and Q5 in a fashion similar to that in which I4 and Q4 were calculated, will always make Q5 equal to zero. With this value of $\theta$, the calculated value of I5 will correctly represent the spatial derivative of the density in the direction of propagation. The angle needed for the calculation of I4 and Q4 was based on the assumption of absolutely constant velocity of propagation in the medium being scanned. No such basis is available for determining the value of $\theta$, but for large reflections from distinct interfaces, it can be calculated easily from the values of I4 and Q4 at the peak of the reflection, by 24 through 27 in FIG. 6. A comparator, 28, selects the value calculated from the smaller of the tangent and cotangent functions, in order to assure good accuracy for any angle.

Figure 1:
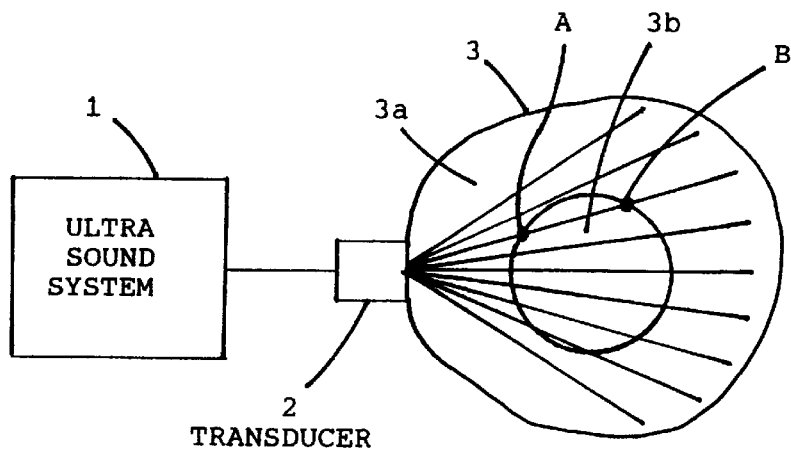
FIG. 1 shows the sector scan geometry used as a basis for the discussion.

The values of I4 and Q4 for all the points of a complete scan, comprising all of the lines shown in FIG. 1, are stored in two rectangular memory arrays, 29 and 30 in FIG. 7, with each row representing one scan line, and the columns representing successive points along the lines. The values of $\theta$, at the times of large reflections, are stored in a third memory array, 31, with the same geometry. The times at which the reflected signal is large enough to warrant storing the angle are determined by a comparator, 32, with an appropriate threshold level as one input, and the square of the value of the reflected signal as the other. This last signal is simply the sum of the squares of I4 and Q4, and is developed by components 33 to 35. The comparator output will be positive only when there is a large reflection from a distinct interface, allowing accurate determination of the phase angle.

Figure 8:
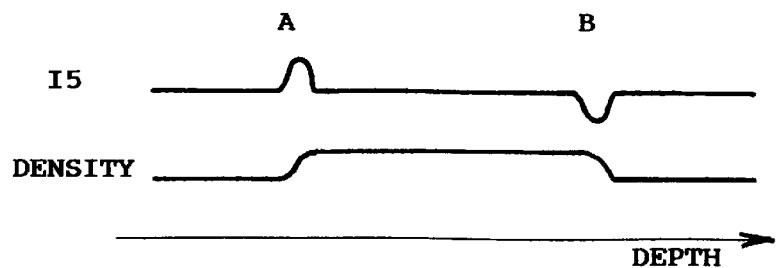
FIG. 8 shows two waveforms produced by the sub-system of FIG. 7.

Following completion of the scan, the values of $\theta$ for all other points in the $\theta$ memory array are determined with standard two dimensional interpolation and smoothing programs, 36, to provide a complete phase map, 37. Then I5 is calculated for each point from all three stored values by components 38 to 42. Since the values of $\theta$ have been determined so as to make Q5 equal to zero at all points, it is of no interest and there is no need to calculate it. The values of I5 along each scan line are then integrated by integrator 43 to give the final output from this stage of the processing, designated DENSITY in FIG. 7. Values of I5 and DENSITY for the scan line containing points A and B in FIG. 1 are shown in FIG. 8. The integrator is reset to zero or any other desired value at the beginning of each line.

Although some of the processing functions shown in FIG. 6 and FIG. 7 could be handled satisfactorily with analog modules, the storage and interpolation functions are practical only with digital processing in a computer or other type of digital signal processor. Therefor the most practical implementation of this entire stage of processing, and probably everything following the development of I1 and Q1, is digital processing of some type.

The interpolation of phase between any two points along a scan line at which the phase can be calculated from 14 and Q4 will be incorrect if the difference in phase between those two points exceeds $2\pi$ radians, because the method of calculation shown in FIG. 6 provides only values up to $2\pi$ radians. If necessary, values of $\theta$ at points farther along scan lines in the partial $\theta$ phase map can be augmented by positive or negative integral multiples of $2\pi$, until it is evident from the appearance of the final image that the phase map of $\theta$ is correct. Such augmentation initially has to be done by operator intervention through a suitable software program. If it is found that for certain typical scanning situations the augmentation required is usually the same, the augmentation constants could be stored and applied automatically with appropriate software.

Theoretically, the phase correction processing utilized to develop I4 and Q4, and the subsequent processing to develop I5, could be consolidated into one process. That approach would be a minor variation of the invention, but would probably be more difficult to implement.

When a real time display is desired, and the image is not changing with time too rapidly, the phase map developed from the information in one scan can be used with the I4 and Q4 signals from subsequent scans to provide an I5 signal, with negligible delay. New values of $\theta$ can be calculated off line from the data from any scan to provide updating of the phase map as often as possible, ideally for every scan. Under these conditions it would be possible to dispense with the storage of I4 and Q4. It may also be desirable to do some temporal averaging of the phase map, particularly when the image is not changing very rapidly.

As values of DENSITY are determined, they can be stored in a rectangular array with the same geometry as the I4, Q4, and $\theta$ arrays. This may or may not be the same geometry as the scan, depending on the type of raster scan utilized. For the sector scan geometry of FIG. 1, the geometry will not be the same, and a conversion will have to be made before displaying the data in order to have a geometrically correct image. This operation is well established in the prior state of the art of medical diagnostic imaging and does not need to be discussed here.

After any necessary conversion, but before display, standard two dimensional image processing functions can be performed on the data if desired. This is the proper location for adjustment of brightness and contrast, and for filtering or edge enhancement. It may also be desirable to perform some special image processing functions to minimize shading across the image. Shading is normally dealt with mainly by fine adjustment of the gain versus time program of the amplifier directly following the transmit/receive switch. The integration utilized in this invention is apt to aggravate the shading problem, and shading cannot be corrected perfectly by adjustment of the gain program alone, in any case. That is because the angle of an interface relative to the direction of propagation, the location of the reflection, and other factors, all affect the amplitude of the reflected signal incident on the transducer, in addition to the effect of attenuation. The image information gives the location of major reflections and one component of the angle of incidence, allowing partial correction to be made through an appropriate special purpose image processing program.

If an interface is in motion, the reflection will experience a Doppler frequency shift that allows the velocity component along the direction of propagation to be calculated in several ways that are well established in the prior art. The shift in frequency encountered in ordinary medical diagnostic imaging is so small that it will not alter the phase enough during the few cycles of the excitation pulse to cause a problem for the coherent detection process of this invention.

Although the present invention has been described with reference to particular means, material, and embodiments, from the foregoing description, one skilled in the art can easily ascertain the essential characteristics of the present invention and various changes and modifications may be made to adapt to various uses and conditions without departing from the spirit and scope of the invention. The invention is defined in the following claims.

What I claim as my invention is:

1. An ultrasonic imaging system that comprises:

conventional diagnostic imaging system components such as transmit/receive switch, transducer, programmable gain amplifier, scanning mechanism, and display;

a pulse generator that generates a short burst of sinusoidal excitation;

multipliers and a ninety degree phase shifter to generate initial in-phase and quadrature coherently detected signals;

a sub-system for removing, to a first order, the effect that the position of a reflection in the object being scanned has on the in-phase and quadrature detected signals, as a result of the phase shift resulting from transit time which is a function of the depth at which a reflection occurs;

a sub-system for determining the final fine phase correction angle needed, from the relative amplitudes of the intermediate in-phase and quadrature components at reflections of high amplitude;

means for determining the points at which the reflected signal amplitude is sufficient to allow reliable determination of the final fine phase correction angle;

means for storing intermediate values of in-phase and quadrature coherently detected signals, and such values of the final fine phase correction as are available, for one complete scan;

a means for interpolating values of the final fine phase correction for all points of the scan;

a sub-system for determining a value for each point, from the stored values of the intermediate in-phase and quadrature coherently detected signals, and the final fine phase correction angle at each point;

an integrator to integrate these values along each scan line to give a value proportional to a function of density and elastic constants.

2. An ultrasonic imaging system according to claim 1, wherein said sub-systems preserve the polarity of parameter changes while rejecting dependence on the position at which a reflection occurs.

3. An ultrasonic imaging system according to claim 1, wherein the final coherently detected signal is integrated to provide a display of a function of density and elastic constants, rather than the derivative of that function in the direction of propagation of the ultrasonic wave.

4. A sub-system for removing, to a first order, the effect that the position of a reflection in the object being scanned has on the in-phase and quadrature detected signals, as a result of the phase shift resulting from transit time which is a function of the depth at which a reflection occurs.

5. Means according to claim 4 for compressing the in-phase and quadrature signals as initially coherently detected.

6. Means according to claim 4 for multiplying the compressed signals by sine and cosine signals of twice the frequency of the excitation pulse.

7. Means according to claim 4 for combining the four products into in-phase and quadrature signals with most of the position dependence removed.

8. A sub-system for making a final fine phase correction.

9. Means according to claim 8 for determining values of an angle that allows complete phase correction of the data, at points of the scan where there is a large reflection from a distinct interface.

10. Means according to claim 8 for interpolating in two dimensions the values of the necessary correction angle at all other points of the scan.

11. Means according to claim 8 for utilizing the fine phase correction angle to combine the intermediate in-phase and quadrature signals so as to provide a final coherently detected signal which is independent of position.

* * * * *